(12) United States Patent
Harmache et al.

(10) Patent No.: US 8,859,276 B2
(45) Date of Patent: Oct. 14, 2014

(54) **RECOMBINANT *NOVIRHABDOVIRUSES* AND USES THEREOF**

(75) Inventors: Abdallah Harmache, Trappes (FR); Michel Bremont, Choisy-le-Roi (FR); Joseph Koumans, La Wageningen (NL)

(73) Assignee: Institut National de la Recherche Agronomique, Paris (FR)

( * ) Notice: Subject to any disclaimer, the term of this patent is extended or adjusted under 35 U.S.C. 154(b) by 1073 days.

(21) Appl. No.: 12/304,812

(22) PCT Filed: Jun. 15, 2007

(86) PCT No.: PCT/IB2007/002756
§ 371 (c)(1), (2), (4) Date: Mar. 11, 2009

(87) PCT Pub. No.: WO2007/144773
PCT Pub. Date: Dec. 21, 2007

(65) Prior Publication Data
US 2009/0208529 A1      Aug. 20, 2009

(30) Foreign Application Priority Data

Jun. 16, 2006   (EP) .................................. 06290982

(51) Int. Cl.
| | |
|---|---|
| *C12N 15/63* | (2006.01) |
| *C12N 15/00* | (2006.01) |
| *C12N 15/09* | (2006.01) |
| *C12N 15/11* | (2006.01) |
| *C12N 15/86* | (2006.01) |
| *C12N 7/00* | (2006.01) |

(52) U.S. Cl.
CPC ...... *C12N 15/86* (2013.01); *C12N 2760/20021* (2013.01); *C12N 2760/20043* (2013.01); *C12N 7/00* (2013.01)
USPC ....... 435/320.1; 435/70.1; 435/455; 536/23.1

(58) Field of Classification Search
None
See application file for complete search history.

(56) References Cited

PUBLICATIONS

Brémont, M. "Reverse Genetics on Fish Rhabdoviruses: Tools to Study the Pathogenesis of Fish Rhabdoviruses" CTMI, 292: 119-141, 2005.
Harmache, Abdallah et al. "Bioluminescence Imaging of Live Infected Salmonids Reveals that the Fin Bases Are the Major Portal of Entry for *Novirhabdovirus*" Journal of Virology, 80: 3655-3659, 2006.
Thoulouze, Maria-Isabel et al. "Essential Role of the NV Protein of *Novihabdovirus* for Pathogenicity in Rainbow Trout" Journal of Virology 78: 4098-4107, 2004.
Biacchesi, Stéphane et al. "Recovery of NV Knockout Infectious Hematopoietic Necrosis Virus Expressing Foreign Genes" Journal of Virology, 74: 11247-11253, 2000.
Alonso, Marta et al. "The NV Gene of *Snakehead Rhabdovirus* (SHRV) Is Not Required for Pathogenesis, and a Heterologous Glycoprotein Can Be Incorporated into the SHRV Envelope" Journal of Virology 78: 5875-5882, 2004.

*Primary Examiner* — Celine Qian
(74) *Attorney, Agent, or Firm* — Morgan, Lewis & Bockius LLP

(57) ABSTRACT

The invention relates to recombinant novirhabdoviruses having at least one sequence encoding a polypeptide of interest added to their genome. Said recombinant novirhabdoviruses are useful as gene vectors, for producing recombinant proteins, or for producing vaccines for fish or for higher vertebrates.

13 Claims, 11 Drawing Sheets

Wild-type IHNV sequence

End of M ORF

..........GGGGGAAGGAAAAA TAGGAGTCGACCATGCCGTCTCTCACTCACCCATCCATCGGCCGCAA
         G  K  E  K                                                    EagI

CCCTCCTCCATCCCCAGAGTCCCTCCACTCCTCACTCCGT CCAAGACAGAAAAAAA TG...............  .G gene
                                         Transcription Stop Additional cassette EagI      Transcription Stop   Transcription Start  SpeI                              SmaI
CGGCCG CCAAGACAGAAAAAAA TGGCACTTTTGTGCACTAGT ATGgene of interestTAG CCCGGG EagI
CGGCCGACCCAACCCTCCTCCATCCCCAGAGTCCCTCCACTCCTCACTCCGT CCAAGACAGAAAAAAA TG...
                                                     Transcription Stop ..............  .G gene

Figure 2

| IHNV<br>E3E2<br>6KE1 | IHNV<br>Cap<br>E3E2 | IHNV<br>6KE1 | IHNV |

SDV-E1 →

— (76-Kd)

— (50-Kd)

— (26-Kd)

| 1 | 2 | 3 | 4 |

Figure 4

| IHNV<br>Infected cell | IHNV-HA<br>Infected cell |

HA dimer

HA
(42-kDa)

| 1 | 2 |

Figure 5

| IHNV | IHNV $G_{VHSV}$ | IHNV $G_{VHSV}$ $LUC_{RR}$ | IHNV $G_{VHSV}$ EGFP | Mock |

— (83-Kd)

← G-VHSV

Anti IPNV VP2          Anti ISAV HA

RECOMBINANT *NOVIRHABDOVIRUSES* AND USES THEREOF

RELATED APPLICATIONS

The present application is a U.S. National Phase Application of International Application PCT/IB2007/002756, filed Jun. 15, 2007, which claims the benefit of European Application No. 06290982.5, filed Jun. 16, 2006, all of which are herein incorporated by reference in their entirety.

The present invention relates to the use of novirhabdoviruses as a gene vector, for producing recombinant proteins, or for producing vaccines useful in fish or in higher vertebrates.

Novirhabdoviruses are negative-strand RNA viruses of the Rhabdoviridae family.

The Novirhabdovirus genus comprises various pathogenic species for aquatic animals, in particular for fish.

The structure of the novirhabdoviral genome is similar to that of mammalian rhabdoviruses, but differs therefrom by the presence of an additional gene, encoding a non-structural protein, called NV (for "non-virion") protein, the function of which remains unknown at the current time.

The novirhabdoviral genome comprises six genes, the organization of which can be represented diagrammatically as follows:

3'-N-P-M-G-NV-L-5'

N represents the gene encoding the nucleoprotein associated with the viral RNA, P represents the gene encoding the phosphoprotein associated with the viral polymerase, M represents the gene encoding the matrix protein, G represents the gene encoding the envelope glycoprotein G, NV represents the gene encoding the NV protein, and L represents the gene encoding the RNA-dependent viral RNA polymerase.

These genes are separated by intergenic regions: each of them comprises a transcription termination/polyadenylation signal and a transcription initiation signal, which allow the transcription of the genes into individual mRNAs, separated by an untranscribed intergenic dinucleotide.

The type species of the genus is Infectious Hematopoietic Necrosis Virus (IHNV) which is the etiological agent of a serious disease in several species of salmonids, mainly in yearling trouts. Other species in the genus include Hirame rhabdovirus (HRV), Viral Haemorrhagic Septicaemia Virus (VHSV), and Snakehead rhabdovirus (SKRV). The complete genomic sequence of IHNV is available in GenBank under accession number L40883; the complete genomic sequence of VHSV is available in GenBank under accession number Y18263; the complete genomic sequence of HRV is available in GenBank under accession number AF104985; the complete genomic sequence of SKRV is available in GenBank under accession number AF147498.

Recombinant novirhabdoviruses can be obtained by reverse genetics, by co-transfecting a host cell with an antigenomic complementary DNA (antigenomic cDNA), i.e. a positive-sense copy of the viral genome, and with DNA molecules encoding the N, P and L viral proteins (BIACCHESI et al., J Virol, 74, 11247-53, 2000), and modify their genome.

This approach has also allowed different modifications to the novirhabdoviral genome. For instance, it has been shown that the NV gene of the IHN virus can be deleted and replaced by a foreign gene (BIACCHESI et al., 2000, cited above; THOULOUZE et al., J Virol, 78, 4098-107, 2004; PCT WO 03/097090). It has also been shown that it was possible to replace the major structural proteins (M and G) of IHNV with those of VHSV (BIACCHESI et al., J Virol, 76, 2881-9, 2002).

It has also been tried to insert an additional gene in a novirhabdovirus. (BIACCHESI, Doctorate Thesis: "GENERATION DE RHABDOVIRUS AQUATIQUES RECOMBINANTS PAR GENETIQUE INVERSE", UNIVERSITE PARIS XI ORSAY, 5 Apr. 2002). A DNA construct containing a foreign gene (encoding rainbow trout IL-1-β) flanked by a transcription initiation signal and a transcription termination/polyadenylation signal recognized by the viral L polymerase, was inserted in the IHNV cDNA, in the intergenic region between the M and G genes of IHNV. More specifically, since this gene was introduced in a naturally occurring EagI restriction site situated between the end of the M ORF and the transcription termination signal of the M gene, this construct comprised a sequence (CCAAGACA-GAAAAAAATGGCAC; SEQ ID NO: 1) consisting of the predicted transcription termination/polyadenylation site of the M gene of IHNV (CCAAGACAGAAAAAA; SEQ ID NO: 2) followed by the non-transcribed intergenic dinucleotide TG and by the transcription initiation sequence GCAC, said sequence being immediately followed by the ORF of the IL-1-β flanked in 5' by a SpeI restriction site, and in 3' by a SmaI restriction site.

The recombinant virus (IHNV-IL-1) thus obtained was able to multiply normally in cell culture and was as pathogenic in juvenile rainbow trouts as the wild type IHNV. However, only IL-1-β mRNA, but not IL-1-β protein was detected in the infected cells. On the other hand, a similar recombinant IHNV, containing a gene encoding the green fluorescent protein (GFP), accompanied by the same transcription initiation signal and the same transcription termination/polyadenylation signal was able to express GFP in the infected cells (BREMONT, Current Topics in Microbiology and Immunology 292: 119-141, 2005).

BRIEF DESCRIPTION OF THE DRAWINGS

FIG. 2 depicts that the PCR product was digested with EagI enzyme and inserted into the EagI site of pIHNV, leading to the pIHN-LUC construct.

FIG. 4 shows Western blot results using a monoclonal antibody directed against SDV-E1 glycoprotein (Lane 1: IHNV-E3E26KE1; Lane 2: IHNV-CapE3E2; Lane 3: IHNV-6KE1; Lane 4: wild type IHNV).

FIG. 5 shows Western blot results using a polyclonal antibody directed against ISAV-HA glycoprotein (Lane 1: wild type IHNV; Lane 2: IHNV-ISAV HA)

FIG. 6 shows Western blot results using a monoclonal antibody directed against VHSV G glycoprotein (Lane 1: wild type IHNV; Lane 2: IHNV-$G_{VHSV}$; Lane 3: IHNV-$G_{VHSV}$/$LUC_{RR}$: Lane 4: IHNV-$G_{VHSV}$/EGFP).

FIG. 7 shows the specific labeling of VP2 protein in the cytoplasm of IHNV-$VP2_{IBDV}$ infected cells.

FIG. 10 demonstrates that the ISAV F protein is incorporated into the recombinant IHNV viral particles.

FIG. 11 shows confocal laser scanning microscopy (CLSM) results (A: IHNV N-EGFP; B: IHNV G-EGFP; C: IHNV M-EGFP; D: IHNV NV-EGFP).

FIG. 16 shows the luciferase expression measured using a luminometer and the Renilla luciferase Assay system.

FIG. 17 shows Western blot results (A: Western blot with the polyclonal antibody directed against the HA glycoprotein of ISAV; B: Western blot with the serum of mice inoculated with recombinant IHNV 3C1).

Figure 1:
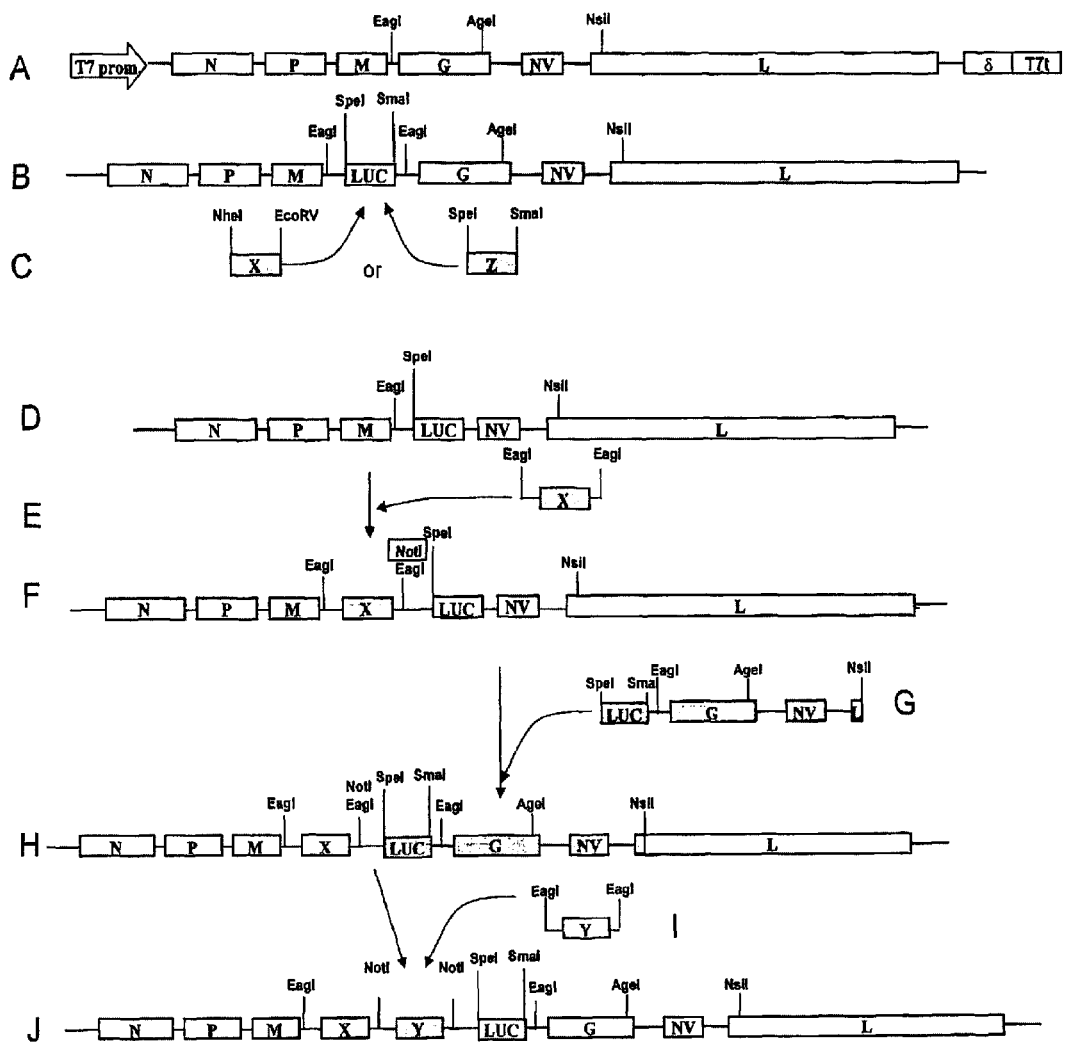
FIG. 1 depicts the following constructs: A: initial pIHN construct containing the full length IHNV cDNA genome, B: pIHN-LUC, C: pIHN-X, D: pIHN-LUC-ΔG, E: insert generated through restriction of pIHN-X with EagI, F: pIHN-X-LUC-ΔG, G: insert generated through digestion of pIHN-LUC by SpeI/NsiI (17 prom=T7 RNA polymerase promoter, Δ=ribozyme hepatitis delta sequence, T7t=T7RNA polymerase terminator sequence), H: PIHN-X-LUC, I: insert EagI/EagI generated through digestion of pIHN-Y, J: pIHN-X-Y-LUC.

The inventors have now discovered that when the transcription initiation sequence GCAC disclosed by BIACCHESI or BREMONT is replaced by the sequence GCACTTTTGTGC (SEQ ID NO: 3), the additional gene is not only transcribed but also translated, independently of its nature, allowing the expression of a broad range of foreign proteins.

The present invention thus provides recombinant novirhabdoviruses having one or more additional transcription units inserted into at least one of the intergenic regions of the genome of a host novirhabdovirus. The invention also provides recombinant DNA constructs allowing to obtain said recombinant novirhabdoviruses.

A "transcription unit" (also designated herein as a "cistron") is herein defined as a DNA construct comprising a transcription initiation signal, followed by an ORF encoding a protein of interest, and by a transcription termination/polyadenylation signal.

The invention relates to a recombinant DNA construct comprising:
a) a region comprising a transcriptional termination/polyadenylation sequence of a novirhabdovirus gene;
b) a region comprising a transcription initiation sequence of a novirhabdovirus gene;
said region a) being followed or said region b) being preceded by a non-transcribed intergenic dinucleotide of a novirhabdovirus,
c) a region comprising an open reading frame encoding a protein of interest.

The termination/polyadenylation sequence of region a) and the initiation sequence of region b) can be derived from a same gene or from two different genes of a novirhabdovirus. Preferably, they are derived from one or two gene(s) of the novirhabdovirus wherein it is intended to insert the construct.

The non-transcribed intergenic dinucleotide is preferably selected among TG, and CG.

Preferably, a subject of the present invention is a recombinant DNA construct comprising:
a) a region comprising a transcriptional termination/polyadenylation sequence derived from the M gene of a novirhabdovirus, said region being defined by the following sequence: VHHAGAYAGAAJAAAA (SEQ ID NO: 4), wherein A, T, G, V, H, and Y have their usual meaning in the IUPAC nucleotide code;
b) a region comprising a transcription initiation sequence derived from the G gene of a novirhabdovirus, said region being defined by the following sequence: GCACDWK-WGTGY (SEQ ID NO: 5), wherein A, T, G, C, D, W, K, and Y have their usual meaning in the IUPAC nucleotide code;
said region a) being followed and/or said region b) being preceded by the dinucleotide TG;
c) a region comprising an open reading frame encoding a polypeptide of interest.

According to a preferred embodiment, the termination/polyadenylation sequence of region a) and the initiation sequence of region b) are derived from the novirhabdovirus wherein it is intended to insert the construct, and preferably are respectively derived from the M and G gene of said novirhabdovirus.

For instance, if it is intended to insert the construct in IHNV, the termination/polyadenylation sequence will be CCAAGACAGAAAAAAA (SEQ ID NO: 2), and the transcription initiation sequence will be GCACTTTTGTGC (SEQ ID NO: 3).

In the same way, if it is intended to insert the construct in VHSV, the termination/polyadenylation sequence will be ATTAGATAGAAAAAAA (SEQ ID NO: 6), and the transcription initiation sequence will be GCACATTTGTGT (SEQ ID NO: 7); if it is intended to insert the construct in HRV, the termination/polyadenylation sequence will be ATCAGATAGAAAAAAA (SEQ ID NO: 8), and the transcription initiation sequence will be GCACATTTGTGT (SEQ ID NO: 7); if it is intended to insert the construct in SKRV, the termination/polyadenylation sequence will be GAAAGACAGAAAAAAA (SEQ ID NO: 9), and the transcription initiation sequence will be GCACGAGAGTGC (SEQ ID NO: 10).

In region c) the open reading frame encoding the polypeptide of interest may optionally be fused to an open reading frame encoding a novirhabdoviral structure protein (i.e N, P, M, or G), preferably protein N. The fusion allows the incorporation of the polypeptide of interest in the novirhabdoviral particle. Preferably, the N-terminus of the polypeptide of interest is fused to the C-terminus of said novirhabdoviral structure protein.

However, when the protein of interest which is expressed in a novirhabdovirus of the invention is a membrane protein, such as a membrane glycoprotein of an enveloped virus, it can be incorporated in the viral particle, without need to fuse it to a novirhabdoviral structure protein.

The order of the regions a) b) and c) in the DNA construct depends on the position where one intends to insert said construct into the intergenic region of the host novirhabdovirus.

If the construct is to be inserted between the end of an endogenous ORF and the transcription termination/polyadenylation signal of the corresponding endogenous gene, the order will be a-b-c. In this case, the transcription of the endogenous gene will be terminated at the termination/polyadenylation sequence of region a) of the construct, and the transcription of the ORF encoding the protein of interest will be initiated at the initiation sequence of region b) of the construct and terminated at the endogenous termination/polyadenylation signal of the endogenous gene.

If the construct is to be inserted between the transcription initiation signal and the start codon of an endogenous gene, the order will be c-a-b. In this case, the transcription of the ORF encoding the protein of interest will be initiated at the initiation signal of the endogenous gene, and terminated at the termination/polyadenylation sequence of region a), and the transcription of the endogenous gene will be initiated at the initiation sequence of region b) of the construct.

If the construct is to be inserted between the transcription termination/polyadenylation signal of a first endogenous gene, and the transcription initiation signal of a second endogenous gene, the order will be b-c-a. In this case, the transcription of the ORF encoding the protein of interest will be initiated at the initiation sequence of region b), and terminated by the termination/polyadenylation sequence of region a) of the construct.

The present invention also provides an antigenomic cDNA of the genome of a novirhabdovirus, characterized in that it contains one or more recombinant DNA constructs of the invention inserted in a portion of said cDNA comprised between the stop codon of a first endogenous ORF and the start codon of a second endogenous ORF of a host novirhabdovirus.

According to a preferred embodiment, said antigenomic cDNA contains two constructs of the invention inserted in a portion of said cDNA comprised between the stop codon of a first endogenous ORF and the start codon of a second endogenous ORF; according to still another preferred embodiment, said antigenomic cDNA contains three constructs of the invention inserted in a portion of said cDNA comprised between the stop codon of a first endogenous ORF and the start codon of a second endogenous ORF.

Preferably the first endogenous ORF is the M ORF, and the second endogenous ORF is the G ORF.

The present invention also provides a recombinant novirhabdovirus containing a genomic RNA complementary to an antigenomic DNA of the invention.

The invention also relates to the use of recombinant novirhabdoviruses having one or more additional transcription units inserted into at least one of the intergenic regions of the genome of a host novirhabdovirus, for producing proteins of interest in vertebrate cells (preferably fish cells) in culture, and/or for obtaining vaccines.

The inventors have found that, when containing one construct, novirhabdoviruses of the invention are able to multiply normally in fish cells in culture and keep their pathogenic capacity. When a second construct is added, the ability to multiply in cell cultures is conserved, while the pathogenicity is diminished. The addition of a third construct has no significant effect on the ability to multiply in cell cultures; typically, the recombinant novirhabdovirus of the invention, comprising one, two, or three constructs, can be produced in cell cultures at titers >$10^8$ p.f.u/ml. On the other hand, recombinant novirhabdovirus of the invention, comprising three constructs have a considerably reduced pathogenicity.

For the production of proteins of interest in cells in culture, one can use a novirhabdovirus containing one or more constructs, preferably two or three constructs.

The use of a novirhabdovirus of the invention having two or more constructs is of particular interest if one wishes to express simultaneously several polypeptides, for instance sub-units of a same enzyme, or an inactive precursor of an active protein, and a second protein able to convert said precursor into the active form. In vaccine development some protective epitopes are formed only when two or more polypeptides are expressed simultaneously. The use of a novirhabdovirus of the invention will allow such polypeptides to be expressed in order to form the protective epitopes.

Further, as disclosed above, the fact that the expressed proteins can be incorporated in the viral particle, is of particular interest for the production of vaccines.

Novirhabdovirus of the invention containing three or more constructs can be used as live attenuated vaccines, for the vaccination of fish, for instance salmonids in the case of IHNV and VHSV. They can advantageously be administered by balneation, i.e. by simple addition of the vaccine to the water in the breeding tank containing the animals to be immunized.

Alternatively the recombinant novirhabdoviruses or the cells that produce the virus can be used as inactivated vaccine in fish.

The recombinant novirhabdoviruses of the invention, and in particular those that replicate at low temperatures such as IHNV and VHSV, can also be used as a non-replicative antigen delivery system for the vaccination of higher vertebrates, such as birds and mammals. The inventors have indeed observed that when a recombinant IHNV of the invention expressing a foreign antigen is injected in a mammal, said virus is completely unable to replicate in said mammal, while on the other hand, a strong immune response is raised against the foreign antigen incorporated in the viral particle, in complete absence of additional adjuvants.

The inventors have also found that novirhabdovirus that replicate at low temperatures (14 to 20° C.), such as IHNV and VHSV, are particularly suitable for the production of thermosensitive proteins that are difficult to produce in classical expression hosts such as E. coli, baculovirus, yeast, which generally require temperatures of at least 25-30° C. for their growth. They are for instance of particular interest for producing in vitro immunoprotective proteins, useful as vaccine components. Many of these proteins, especially those which originate from fish-pathogenic organisms, cannot be expressed or folded into the right structure at the standard temperature of most bacterial, yeast, eukaryotic and baculovirus-based expression systems.

Thus, an object of the invention is the use of a recombinant IHNV or VHSV comprising a heterologous sequence encoding an antigenic protein of interest, for expressing in vitro said protein in a low temperature expression system.

The invention thus provides a low temperature in vitro expression system, characterised in that said expression system comprises a recombinant IHNV or VHSV comprising at least one heterologous sequence encoding an antigenic protein of interest, and a vertebrate cell susceptible of infection by said recombinant virus and capable of growth at low temperature.

The invention also provides a method for expressing in vitro an antigenic protein of interest, said method comprising:
  infecting a vertebrate cell susceptible of infection by IHNV or VHSV and capable of growth at low temperature with a recombinant IHNV or VHSV comprising at least one heterologous sequence encoding an antigenic protein of interest;
  culturing said cell at a temperature of about 14° C. to about 20° C.;
  recovering the antigenic protein of interest produced by said cell.

According to a preferred embodiment of the invention, said vertebrate cell is a fish cell, for instance an EPC cell.

One can use a recombinant IHNV or VHSV wherein the heterologous sequence is inserted in replacement of an endogenous sequence of the host novirhabdovirus; however, one will preferably use a recombinant IHNV or VHSV wherein the heterologous sequence is inserted in addition to the endogenous sequences of the host novirhabdovirus. Still more preferably, one will use a recombinant novirhabdovirus of the invention, wherein the heterologous sequence is a part of an additional transcription unit inserted into one of the intergenic regions of the host novirhabdovirus. A preferred novirhabdovirus is IHNV.

The present invention will be understood more thoroughly from the further description which follows, which refers to non-limiting examples of construction and of use of recombinant novirhabdoviruses in accordance with the invention.

EXAMPLE 1

Construction of Recombinant Novirhabdoviruses Comprising One, Two, or Three Additional Cistrons in the M-G Intergenic Region FIG. 1 schematically represents the different constructs described below.
Legend of FIG. 1:
A: is the initial pIHN construct containing the full length IHNV cDNA genome. The following elements are represented for this construct and will be omitted in the schemas showing the other constructs: T7 prom=T7 RNA polymerase promoter, δ=ribozyme hepatitis delta sequence, T7t=T7RNA polymerase terminator sequence.
B: pIHN-LUC.
C: pIHN-X.
D: pIHN-LUC-ΔG
E: insert generated through restriction of pIHN-X with EagI
F: pIHN-X-LUC-ΔG.
G: insert generated through digestion of pIHN-LUC by SpeI/NsiI
H: PIHN-X-LUC
I: insert EagI/EagI generated through digestion of pIHN-Y.
J: pIHN-X-Y-LUC
Construction of the Recombinant cDNAs:

The constructions were carried out using the plasmid pIHNV described by BIACCHESI et al. (2000, cited above. This plasmid contains the complete cDNA of the IHN virus genome, cloned downstream of the T7 phage RNA polymerase promoter and upstream of a ribozyme sequence of the hepatitis δ virus and of the T7 phage RNA polymerase transcription terminator, in the vector pBlueScript SK (Stratagene).

pIHNV cDNA genome contains a unique EagI restriction site located in the M-G intergenic region. This restriction site is used to insert an additional cistron, encoding a gene of interest, as schematized in FIG. 1. At the beginning and the end of the gene of interest a SpeI and SmaI restriction enzyme sites have respectively been introduced, to allow the replacement of the gene of interest by another gene. The plasmid pIHNV is schematized in FIG. 1A.
Construction of Recombinant Antigenomic cDNAs with One Additional Cistron
pIHN-LUC (FIG. 1B):

pIHN-LUC results from the insertion of the *Renilla* luciferase expression cassette gene into the EagI site of pIHNV.
It is obtained as follows:
*Renilla* Luciferase gene was PCR amplified from the pBind vector (Promega GenBank, accession number AF264722) using the following oligonucleotides:

EagI SpeI RnLuc:
(SEQ ID NO: 11)
ggggCGGCCGCCAAGACAGAAAAAAATGGCACTTTTGTGCACTAGTAT
GACTTCGAAAGTTTATGATCCA.

This oligonucleotide contain the EagI restriction site (CG-GCCG) followed by the transcription termination/polyadenylation sequence of the M gene (CCAAGACA-GAAAAAAA; SEQ ID NO: 2), by the dinucleotide TG and by the transcription initiation sequence of the G gene (GCACTTTTGTGC; SEQ ID NO: 3) followed by the last 24 nucleotides of the *Renilla* luciferase.

EagI SmaI RnLuc:
(SEQ ID NO: 12)
ggggCGGCCGCCCGGGTTATTGTTCATTTTTGAGAACTCG.

This oligonucleotide contain an EagI restriction site (CG-GCCG).

The PCR product was digested with EagI enzyme and inserted into the EagI site of pIHNV, leading to the pIHN-LUC construct, as shown in FIG. 2.

The final plasmid was sequenced to check the orientation and the sequence of the inserted EagI fragment.

All these plasmids were sequenced to check the orientation and or the sequence of the inserted fragments.
pIHN-X or pIHN-Z (FIG. 1C)

These constructs result from the replacement of the luciferase gene by any other gene of interest (exemplified by X or Z). They are obtained by PCR amplification of the gene of interest with a set of primers containing the SpeI site in one side (or a compatible restriction site like NheI) and in the other side the SmaI site (or a compatible blunt end restriction site).

For pIHN-X, the SpeI/SmaI fragment containing the luciferase open reading frame is replaced with a compatible NheI/EcoRV PCR fragment containing the gene of interest X. The resulting pIHN-X construct has lost the SpeI and the SmaI restriction sites.

Similarly the pIHN-Z construct is obtained from pIHN-Luc by replacement of SpeI/SmaI fragment containing the Luc gene by the SpeI/SmaI PCR fragment containing the Z gene. This construct is termed pIHN-Z.
Construction of Recombinant Antigenomic cDNAs with Two Additional Cistrons
pIHN-X-LUC (FIG. 1D to 1H)

The SmaI/AgeI fragment is removed from the pIHN-LUC plasmid, resulting in the elimination of one of the two EagI site and the deletion of the G gene. The intermediate construct thus obtained is named pIHN-LUC-ΔG (FIG. 1D).

The X expression cassette is obtained by the EagI restriction enzyme digestion of pIHN-X (FIG. 1E).

This insert is ligated with pIHN-LUC-ΔG digested with EagI, resulting in the construct pIHN-X-LUC-ΔG (FIG. 1F). Incidentally after the ligation of the two EagI fragments that led to the pIHN-X-LUC-ΔG construct a unique NotI restriction site is generated between the X and the Luc expression units.

Finally the SpeI/NsiI fragment of the pIHN-X-LUC-ΔG construct is replaced with the corresponding fragment containing the G gene obtained from the pIHN-LUC construct, by digestion with SpeI/NsiI (FIG. 1G). The resulting construct is termed pIHN-X-LUC (FIG. 1H).
Construction of Recombinant Antigenomic cDNAs with Three Additional Cistrons
pIHN-X-Y-LUC (FIGS. 1I and 1J)

The plasmid pIHN-Y is obtained as described for pIHN-X.

pIHN-Y is digested with EagI and the insert EagI/EagI is recovered (FIG. 1I), and inserted in pIHN-X-LUC previously digested with NotI. The construct thus obtained is termed pIHN-X-Y-LUC (FIG. 1J).

pIHN-X-Y-Z

This construct is obtained by replacement of SpeI/SmaI fragment of pIHN-X-Y-LUC containing the Luc gene by the SpeI/SmaI fragment containing the Z gene recovered from pIHN-Z Production of the Recombinant Viruses:

Three expression plasmids comprising respectively the genes encoding the nucleoprotein N, the phosphoprotein P, and the RNA-dependent RNA polymerase L of IHN were constructed, as described by BIACCHESI et al. (2000, publication mentioned above). These constructs are respectively called pT7-N, pT7-P and pT7-L.

The 3 plasmids, pT7-N, pT7-P and pT7-L (at respective doses of 0.25 µg; 0.2 µg and 0.2 µg, and either of the plasmids pIHN-LUC, pIHN-X or Z, pIHN-X-LUC, pIHN-X-Y-LUC, or pIHN-X-Y-Z at the dose of 1 µg are introduced, by transfection in the presence of lipofectamine (GIBCO-BRL), into EPC cells (epithelioma papulosum cyprinid) infected beforehand with a recombinant vaccinia virus expressing the T7 phage RNA polymerase (vTF7-3, FUERST et al. Proc. Natl. Acad. Sci. USA, 92, 4477-4481, 1986).

After transfection, the cells are incubated for 5 hours at 37° C. and then washed with MEM culture medium (without serum) and incubated for 7 days at 14° C. in MEM culture medium containing 2% of fetal calf serum. The cells and the supernatant are frozen/thawed, and clarified by centrifugation for 10 minutes at 10 000 rpm. The supernatant is used at a 1/10 dilution to infect a layer of EPC cells. The viruses are produced in the supernatant 3-4 days post-infection.

Different recombinant INH viruses, having one, two, or three additional cistrons were produced. They are respectively listed in Tables I, II, and III below.

TABLE I

| rIHNV | Cassette | Aim |
|---|---|---|
| CAP | CAP | SDV protection |
| 6KE1 | 6KE1 | SDV protection |

TABLE I-continued

| rIHNV | Cassette | Aim |
|---|---|---|
| CAP-E3E2 | CAP-E3E2 | SDV protection |
| E3E2 | E3E2 | SDV protection |
| E3E2-6KE1 | E3E2-6kE1 | SDV protection |
| IL1β | IL1β | Immuno stimulation |
| $G_{VHSV}$ | $G_{VHSV}$ | VHSV protection |
| ΔG-$G_{VHSV}$ | $G_{VHSV}$ | VHSV protection |
| $LUC_{FF}$ | $LUC_{FF}$ | Bioluminescence |
| $LUC_{RN}$ | $LUC_{RN}$ | Bioluminescence |
| EGFP | EGFP | Reporter protein |
| N-LUCi | N-LUC | Foreign protein incorporation |
| N-EGFP | N-EGFP | Foreign protein incorporation |
| P-Luci | P-Luci | Foreign protein incorporation |
| P-EGFP | P-EGFP | Foreign protein incorporation |
| M-Luci | M-Luci | Foreign protein incorporation |
| M-EGFP | M-EGFP | Foreign protein incorporation |
| $G_{VHSV}$-LUC | $G_{VHSV}$-LUC | Foreign protein incorporation |
| $G_{VHSV}$-EGFP | $G_{VHSV}$-EGFP | Foreign protein incorporation |
| NV-EGFP | NV-EGFP | Foreign protein incorporation |
| NVmyc | NV myc | NV role |
| $HA_{ISAV}$ | HA ISAV | ISAV protection |
| $F5_{ISAV}$ | F5 ISAV | ISAV protection |
| $VP2_{IPNV}$ | VP2 IPNV | IPNV protection |
| $VP2_{IBDV}$ | VP2 IBDV | IBDV protection |

TABLE II

| rIHNV | $1^{st}$ cassette | $2^{nd}$ cassette | Aim |
|---|---|---|---|
| 2C $G_{VHSV}$/LUC | $G_{VHSV}$ | LUC | VHSV protection/Bioluminescence |
| 2C VP2/LUC | $VP2_{IPNV}$ | LUC | IPNV protection/Bioluminescence |
| 2CHA/LUC | HA ISAV | LUC | ISAV protection/Bioluminescence |
| 2C HA/CAP-E3E2 | HA ISAV | CAP-E3E2 | SDV/ISAV protection |
| 2C HA/E3E2-6KE1 | HA ISAV | E3E2-6KE1 | SDV/ISAV protection |

TABLE III

| rIHNV | $1^{st}$ cassette | $2^{nd}$ cassette | $3^{rd}$ cassette | Aim |
|---|---|---|---|---|
| 3C2 $G_{VHSV}$/HA/LUC | $G_{VHSV}$ | VP2 IPNV | LUC | IHNV/VHSV/IPNV protection |
| 3C $G_{VHSV}$/IL1β/LUC | $G_{VHSV}$ | IL1β | LUC | IHNV/VHSV immunostimul. |
| 3C1 HA/F5/LUC | HA ISAV | F5 ISAV | LUC | IHNV/ISAV protection |
| 3C3 HA/VP2/LUC | HA ISAV | VP2 IPNV | LUC | IHNV/ISAV, IPNV protection |
| 3C20 HA/IL1β/LUC | HA ISAV | IL1β | LUC | Immuno-stimulation and IHNV/ISAV protection. |
| 3C14 HA/VP2/CAP-E3E2 | HA ISAV | VP2 IPNV | CAP-E3E2 | IHNV/ISAV/IPNV/SDV protection |
| 3C15 HA/VP2/E3E2-6KE1 | HA ISAV | VP2 IPNV | E3E2-6KE1 | IHNV/ISAV/IPNV/SDV protection |
| 3C10 HA/F5/CAP-E3E2 | HA ISAV | F5 ISAV | CAP-E3E2 | IHNV/ISAV/VHSV protection |

Legend of the tables
SDV: Sleeping Disease Virus
ISAV: Infectious Salmon Anaemia Virus
VHSV: Viral haemorrhagic Septicaemia Virus
IBDV: Infectious Bursal Disease Virus
IPNV: infectious pancreatic necrosis virus
6KE1: SDV E1 glycoprotein gene
CAP: SDV capside gene
E3E2: SDV E2 glycoprotein gene
EGFP: Enhanced green fluorescent protein
F5: ISAV F gene
$G_{VHSV}$: VHSV G glycoprotein gene
HA: ISAV HA gene
IL1β: Interleukin 1 from rainbow trout
$LUC_{FF}$: Firefly luciferase
$LUC_{RR}$: Renilla luciferase
VP2: IPNV VP2 gene
ΔG: deletion of IHNV G gene

EXAMPLE 2

Multiplication in Cell Culture of Recombinant Novirhabdoviruses Comprising One, Two, or Three Additional Cistrons Viral stocks of each of the viruses produced are constituted by successive passages in (EPC) cell culture of the supernatant taken 7 days after transfection (supernatant P0). The cells are infected with 1/100 dilution of the clarified supernatant. After 3 passages, the supernatants are removed, when the cells layer is destroyed by the virus cytopathic effect; this usually occurs 3 to 6 days post-infection. The viral stocks are then titrated by limiting dilution.

Figure 3:
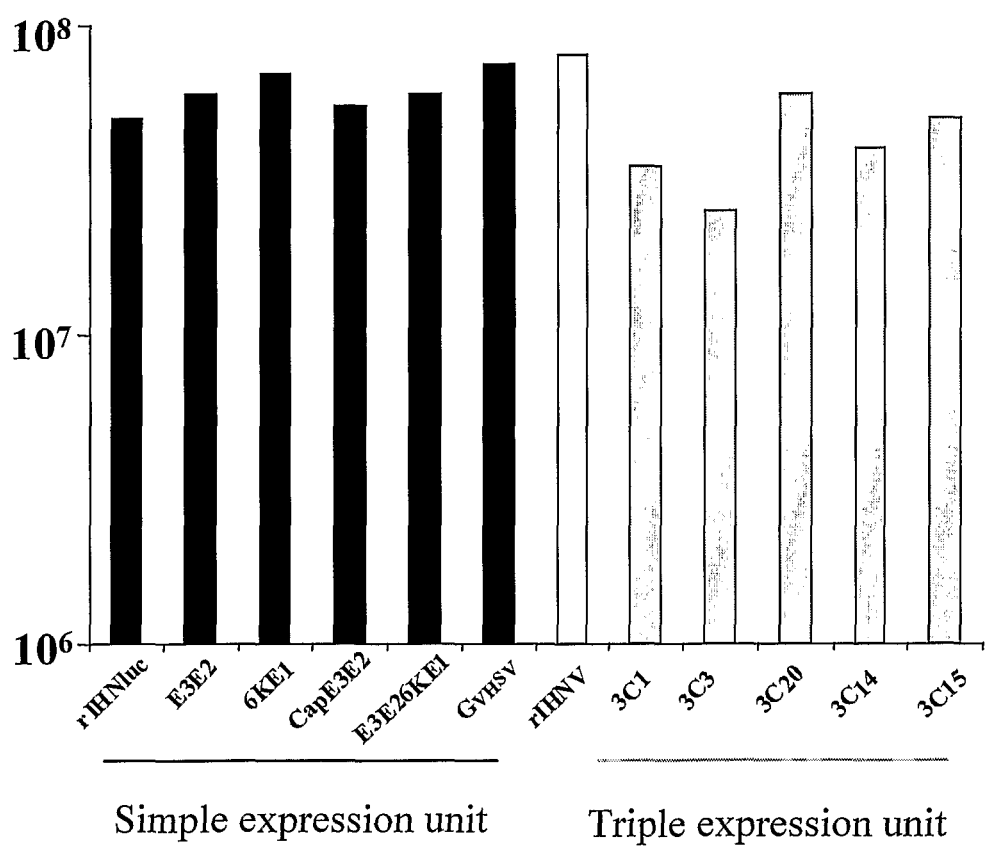
FIG. 3 shows examples of viral titer of various recombinant viruses in EPC cell culture.

FIG. 3 shows examples of viral titer of various recombinant viruses in EPC cell culture. Although the viral titer for all the recombinant viruses is in the same range ($10^8$ PFU/ml), the recombinant viruses comprising three additional expression units have a slower growth compared to the wild type virus. In general it takes six days to get a complete cytopathic effect in EPC cells instead of three days for the wild type IHNV.

EXAMPLE 3

Expression of Proteins of Interest in Recombinant Novirhabdoviruses of the Invention Proteins of interest were produced using the recombinant IHNVs listed in Tables I, II, and III.

Recombinant IHNV Expressing the Sleeping Disease Virus Structural Proteins

EPC cells are infected with wild-type IHNV, IHNV-6KE1, IHNV-CapE3E2, or IHNV-E3E26KE1, at an MOI (multiplicity of infection) of 0.02 (0.02 PFU/cell). The cells are lysed 48 hours post-infection, and the lysates are analyzed by Western blot using a monoclonal antibody directed against SDV-E1 glycoprotein.

The results are shown in FIG. 4: Lane 1: IHNV-E3E26KE1; Lane 2: IHNV-CapE3E2; Lane 3: IHNV-6KE1; Lane 4: wild type IHNV.

Recombinant IHNV Expressing Infectious Salmon Anemia Virus (ISAV) Hemagglutinin (HA) Glycoprotein EPC cells are infected with wild type IHNV, or IHNV-$HA_{ISAV}$, as described above. The cells are lysed 2 days post-infection, and the lysates are immunoprecipitated with anti HA monoclonal antibody and analyzed by Western blot using a polyclonal antibody directed against ISAV-HA glycoprotein.

The results are shown in FIG. 5: Lane 1: wild type IHNV; Lane 2: IHNV-ISAV HA.

Recombinant IHNV Expressing Viral Hemorrhagic Septicemia Virus (VHSV) G Glycoprotein Fused to a Reporter Protein EPC cells are infected, as described above, with wild type IHNV, IHNV-$G_{VHSV}$, IHNV-$G_{VHSV}$/$LUC_{RR}$, IHNV-$G_{VHSV}$/EGFP, or with the supernatant of non-infected EPC cells (mock infected). The cells are lysed 2 days post-infection, and the lysates are analyzed by Western blot using a monoclonal antibody directed against VHSV G glycoprotein.

The results are shown in FIG. 6: Lane 1: wild type IHNV; Lane 2: IHNV-$G_{VHSV}$; Lane 3: IHNV-$G_{VHSV}$/$LUC_{RR}$; Lane 4: IHNV-$G_{VHSV}$/EGFP. The bands observed are consistent with the expected size for respectively VHSV G glycoprotein and the fusion proteins $G_{VHSV}$/$LUC_{RR}$ and $G_{VHSV}$/EGFP.

Recombinant IHNV Expressing VP2 of Infectious Bursal Disease Virus (IBDV)

EPC cells are infected, as described above, with IHNV-$VP2_{IBDV}$ or with the wild type IHNV. 24 hours post-infection the expression of VP2 IBDV is detected using indirect Immunofluorescence assay. The cells are fixed and permeabilized in a bath of $-20°$ C. 50% methanol 50% acetone for 15 minutes in freezer. The fixed cells are then incubated for one hour with 1:400 dilution of a monoclonal antibody directed against VP2 IBDV after a washing step the cells are incubated for 45 minutes with a fluorescein (FITC) conjugated anti-mouse IgG antibody. After a washing step to eliminate unbound antibodies the cells are examined for fluorescein staining with a UV light microscope and photographed with a computer-coupled camera (Nikon).

FIG. 7 shows the specific labeling of VP2 protein in the cytoplasm of IHNV-$VP2_{IBDV}$ infected cells.

No fluorescence can be detected in IHNV infected cells.

Recombinant IHNV Expressing Protein F of ISAV

EPC cells are infected, as described above, with IHNV-$F5_{ISA}$. 36 hours post-infection, the cells are treated for indirect immunofluorescence as described above using an antibody directed against protein F of ISAV.

Figure 8:
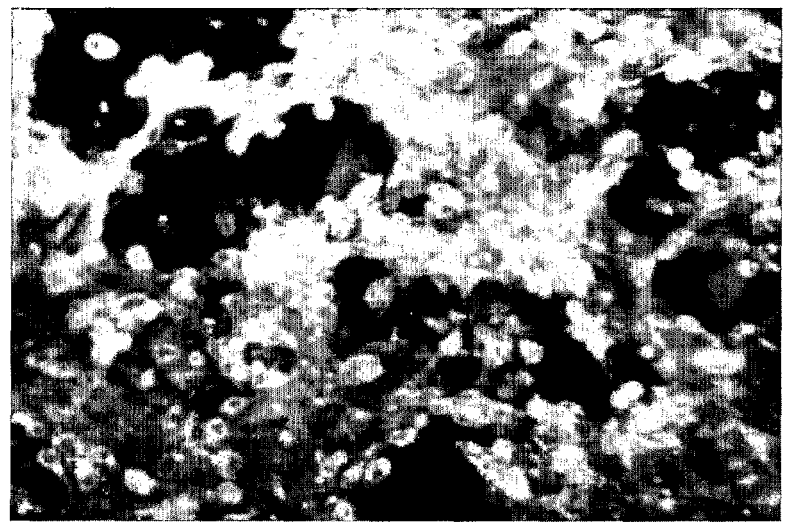
FIG. 8 demonstrates the expression of the ISAV F protein in IHNV-F5$_{ISAV}$ infected cells.

The results shown in FIG. 8 demonstrate the expression of the ISAV F protein in IHNV-$F5_{ISAV}$ infected cells.

Recombinant IHNV Expressing ISAV HA and IPNV VP2

EPC cells are infected, as described above, with IHNV-$3_{C3\ (HA/VP2/LUC)}$. 36 hours post-infection, the cells are treated as described above using a polyclonal antibody directed against protein HA of ISAV and a monoclonal antibody directed against protein VP2 of IPNV. The primary monoclonal antibody is revealed with fluorescein (FITC) conjugated anti-mouse IgG antibody and the primary rabbit polyclonal antibody against protein HA is revealed with TRITC conjugated anti-rabbit antibody.

Figure 9:
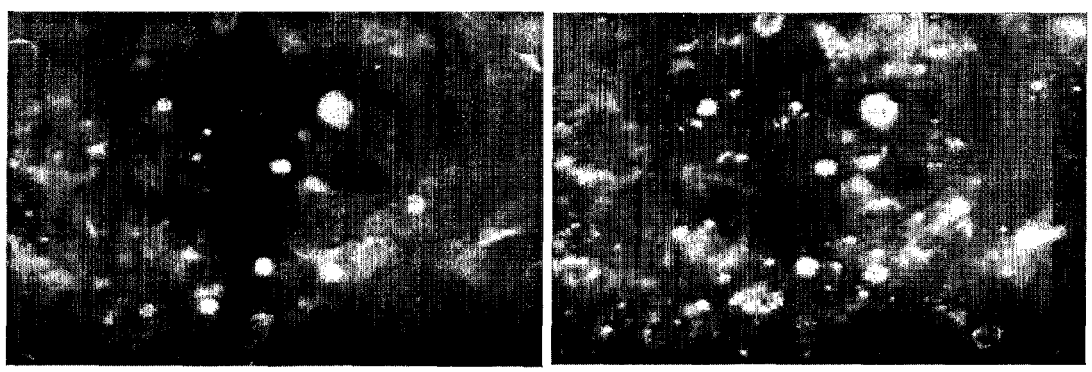
FIG. 9 shows double immunofluorescence staining results (left panel: mAb anti IPNV VP2; right panel: Polyclonal anti ISAV HA).

The results are shown in FIG. 9: left panel: mAb anti IPNV VP2; right panel: Polyclonal anti ISAV HA.

This double immunofluorescence staining shows that IHNV-$3_{C3}$ infected cells express simultaneously the ISAV HA and the IPNV VP2.

EXAMPLE 4

Incorporation of a foreign membrane glycoprotein Into the Recombinant IHNV Viral Particle EPC cells are infected, as described in Example 3, with IHNV-$F5_{ISA}$, or mock infected.

3 days post-infection, the cell-free supernatant is recovered, and the recombinant virus is purified from said supernatant using a sucrose gradient. The purified virus is loaded onto a SDS-PAGE gel. The viral proteins are analyzed by Western blot using a polyclonal antibody directed against ISAV-F glycoprotein. ISAV infected cells were used as a positive control.

Figures 10, 11:
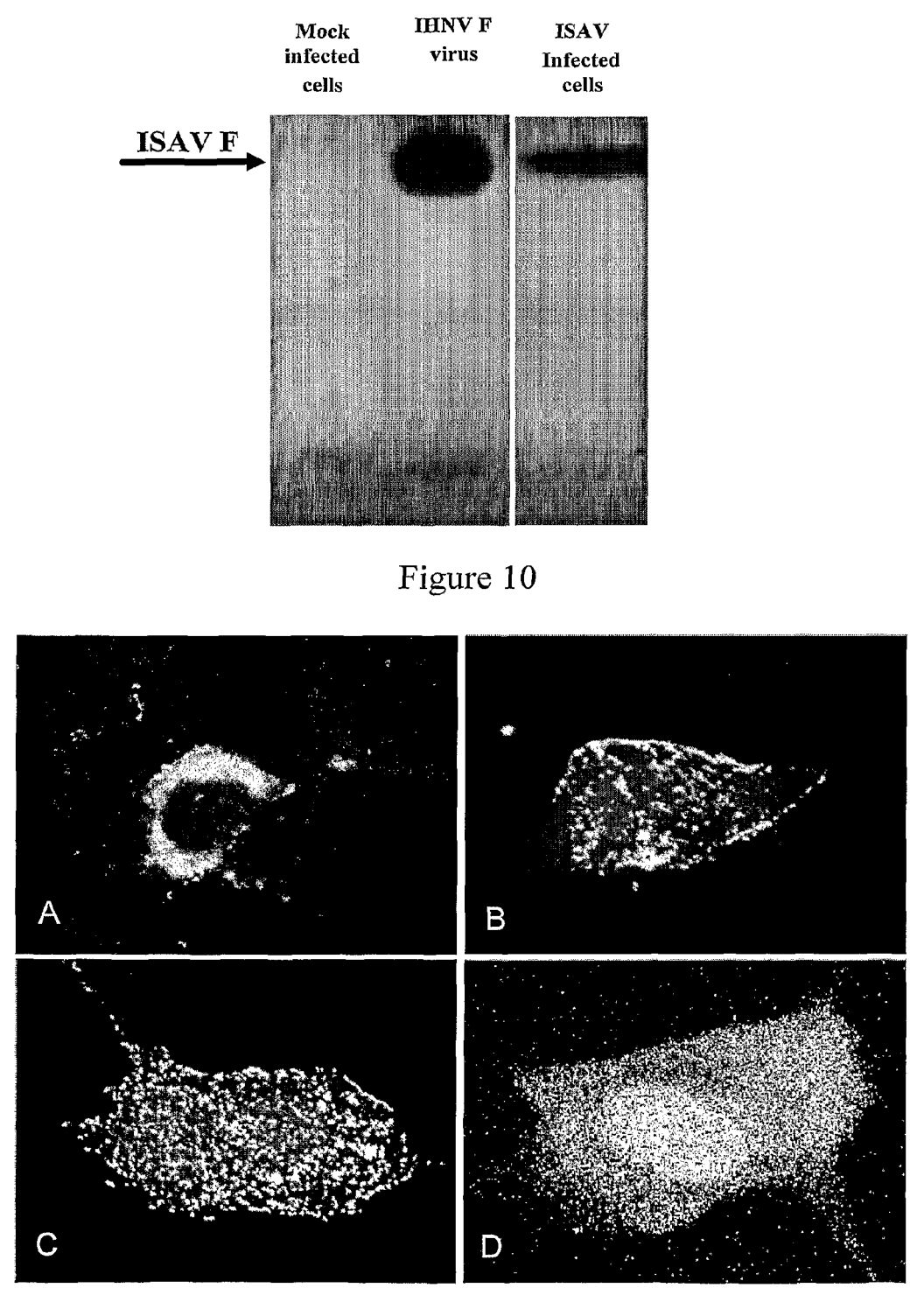

The results are shown in FIG. 10. These results demonstrate that the ISAV F protein is incorporated into the recombinant IHNV viral particles.

Similar results were obtained when incorporation analyses were conducted with ISAV HA and VSHV G glycoprotein respectively in purified IHNV-ISAV HA and IHNV-VSHV G recombinant viruses.

EXAMPLE 5

Incorporation of a Foreign Non-Membrane Protein Into the Recombinant IHNV Viral Particle The possibility to incorporate physically a non-membrane protein into the IHNV viral particle is evaluated using two reporter non-membrane proteins: the EGFP and the *renilla* luciferase.

Chimeric genes encoding either one of the structural proteins of the IHNV virus (N,P,M,G) or the non structural protein NV, fused by its C-terminal end to the N terminal end of the EGFP or of the *renilla* luciferase are constructed.

A SpeI restriction enzyme site was introduced at both ends of each chimeric gene to allow its insertion into the unique SpeI restriction site of the pIHNV LUC or the pIHNV EGFP constructs.

The following constructs were obtained: pIHNV N-EGFP, pIHNV G-EGFP, pIHNV M-EGFP, or pIHNV NV-EGFP pIHNV N-LUC, pIHNV G-LUC, pIHNV P-LUC, pIHNV M-LUC, or pIHNV NV-LUC Recombinant IHNVs are obtained from these constructs, as described in Example 1 above.

Recombinant IHNV Expressing Protein N, G, M, or NV in Fusion with the N Terminal Part of the EGFP EPC cells are infected with IHNV N-EGFP, IHNV G-EGFP, IHNV M-EGFP, or IHNV NV-EGFP. 24 hours post-infection, the cells are directly examined for the expression of the EGFP fusion proteins using a confocal laser scanning microscopy (CLSM).

The results are shown in FIG. 11: A: IHNV N-EGFP; B: IHNV G-EGFP; C: IHNV M-EGFP; D: IHNV NV-EGFP. The G-EGFP and the M-EGFP have membrane localization in accordance with the expected localization of the G and the M proteins, whereas the NV-EGFP seems to accumulate in the nucleus of the infected cells and the N-EGFP is found to be cytosolic.

Recombinant IHNV Expressing Protein N, G, M, or NV in Fusion with the N Terminal Part of the Luciferase EPC cells are infected with IHNV Luc, IHNV N-LUC, IHNV G-LUC, IHNV M-LUC, or IHNV NV-LUC. 4 days post-infection, the cell-free supernatant is recovered, and the recombinant virus is purified from said supernatant using a sucrose gradient. The total protein concentration of each purified virus was measured using a calorimetric dye-binding assay (Bradford). Then one microgram of each purified virus was tested for the luciferase activity in order to determine which structural protein is best suited for luciferase incorporation into the viral particle.

Figure 12:
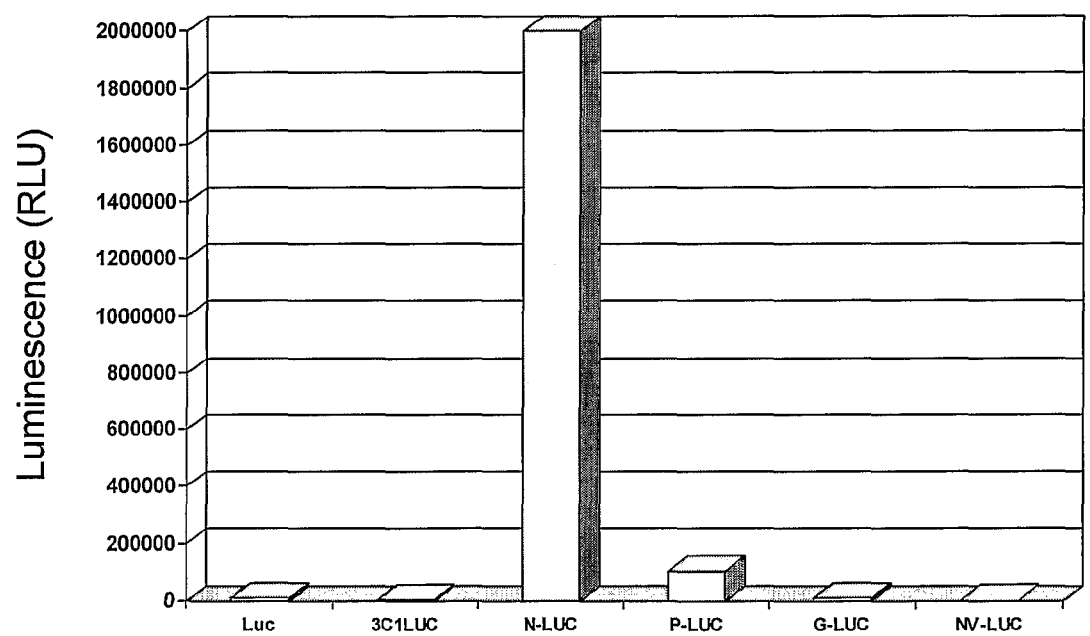
FIG. 12 shows that fusing a foreign non-membrane protein (luciferase in this case) to the N protein is the best strategy for incorporating this protein into the IHNV viral particle.

The result in FIG. 12 shows that fusing a foreign non-membrane protein (luciferase in this case) to the N protein is the best strategy for incorporating this protein into the IHNV viral particle.

EXAMPLE 5

Expression of a Protein of Interest in Living Trouts

Fish are infected by bath immersion with rIHNVLUC, according to the following protocol: the young fish are placed in breeding tanks in a small volume of water (3 liters of water per 100 young fish, average weight 1 g). The rIHNVLUC is added to the water of the tank at a final concentration of $5\times10^4$ PFU/ml (PFU=plaque forming unit). After incubation for 2 hours, the tanks are filled and the water circulation is re-established.

At 4 days post-infection, fish are immersed in a bath containing a luciferase substrate (EnduRen™ Live Cell Substrate, Promega) and submitted to CCD imaging after being anesthetized, in order to evaluate the luciferase activity.

Figure 13:
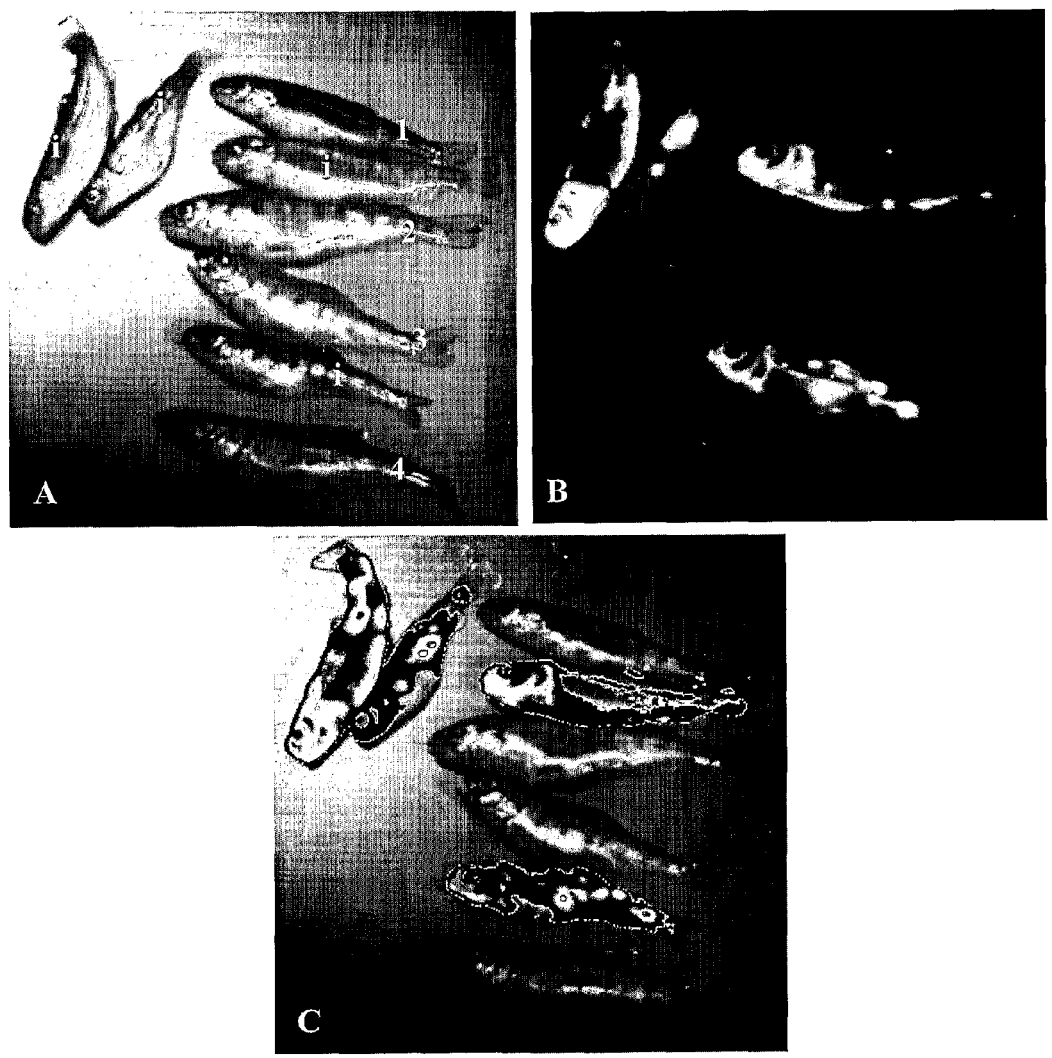
FIG. 13 shows CCD imaging results of fish that are immersed in a bath containing a luciferase substrate after being anesthetized (A: i: rIHNVLUC-infected fish, luciferase substrate bath; 1: mock-infected fish, no luciferase substrate bath; 2: mock-infected fish, luciferase substrate bath; 3: rIHNV-infected fish, luciferase substrate bath; 4: rIHNV-LUC-infected fish, no luciferase substrate bath; B: Original image of the light produced by the renilla luciferase oxidation of its substrate coelenterazine; C: Bioluminescence signals surimposed on the image A).

The results are shown in FIG. 13.

A: i: rIHNVLUC-infected fish, luciferase substrate bath; 1: mock-infected fish, no luciferase substrate bath; 2: mock-infected fish, luciferase substrate bath; 3: rIHNV-infected fish, luciferase substrate bath; 4: rIHNVLUC-infected fish, no luciferase substrate bath.

B: Original image of the light produced by the *renilla* luciferase oxidation of its substrate coelenterazine. The intensity of the emitted light is directly correlated with the level of the *renilla* luciferase expression and with the IHNV-1UC viral replication in the living trout.

C: Bioluminescence signals surimposed on the image A.

EXAMPLE 6

Pathogenicity of the Recombinant Novirhabdoviruses Comprising One or Three Additional Cistrons The pathogenicity of novirhabdoviruses obtained as described in Example 1 above is evaluated by experimental infections in rainbow trout (*Oncorhyncus mykiss*).

The viruses tested are as follows:
rIHNV: wt
rIHNV: 6K-E1 SDV
rIHNV: E3-E2 SDV
rIHNV: Cap-E3-E2 SDV
rIHNV: E3-E2-6K-E1 SDV
rIHNV: LUCRN
rIHNV: G-VSHV
rIHNV 3C1: HA/F5/LUCRN;
rIHNV 3C20: HA/ILB/LUCRN;
rIHNV 3C14: HA/VP2/Cap-E3-E2;
rIHNV 3C15: HA/VP2/E3-E26KE1.

Young trout fish are infected by balneation with $5\times10^4$ PFU/ml of either of these viruses, according to the protocol described in Example 5 above, and the mortality is monitored.

Figure 14:
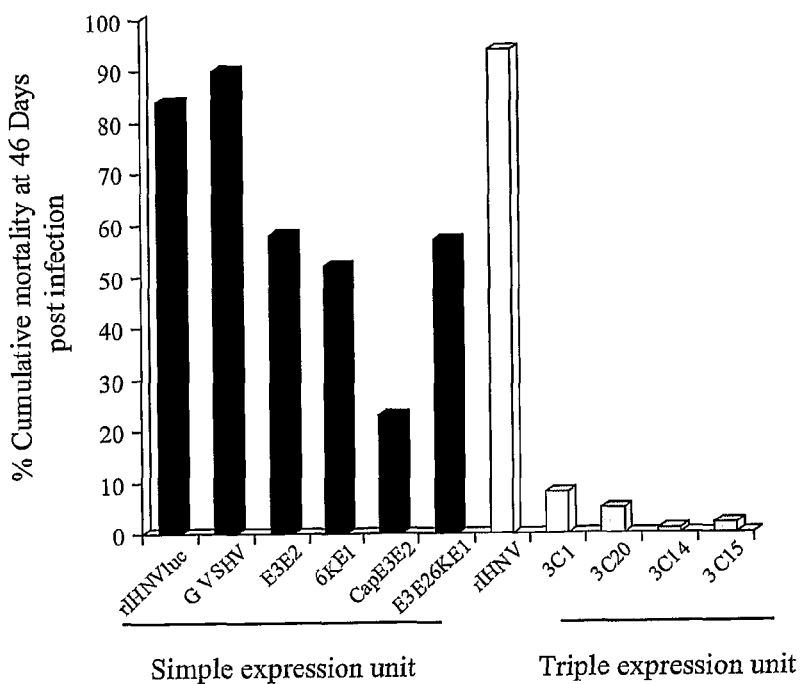
FIG. 14 shows the mortality results of young trout fish that are infected by balneation.

The results are shown in FIG. 14.

These results show that the pathogenicity of the viruses is linked to the number of additional cistrons. While the presence of one additional cistron only induces in most of cases a slight or moderate decrease in pathogenicity, the presence of three additional cistrons induces a drastic attenuation of the pathogenic capacity.

EXAMPLE 7

Vaccine Properties in Fish of the Recombinant Novirhabdoviruses of the Invention In order to establish whether the recombinant viruses attenuated by the presence of three additional cistrons can be used for preparing vaccines, their capacity of protecting young fish against a subsequent challenge with the pathogenic IHNV viral isolate 32/87 was tested.

In a first experiment, young trout fish immunized by balneation with rIHNV 3C1, 3C20, 3C14, or 3C15, under the same conditions as in the pathogenicity trials described in Example 6, are challenged, with IHNV 32/87 either by balneation 46 days later, or by intraperitoneal injection two months later. The mortality is monitored over a period of 58 days.

Challenge by Balneation:

46 days after having received either IHNV 3C1, 3C20, 3C14, or 3C15, or nothing the fish are infected by balneation with $10^5$ pfu/ml of IHNV 32/87.

Challenge by Injection:

Two months after having received either IHNV 3C1, or a mock immunization, batches of 20 young trout the vaccine candidate recombinant are challenged by intraperitoneal injection with the pathogenic IHNV viral isolate 32/87 ($10^6$ pfu/fish).

Figure 15:
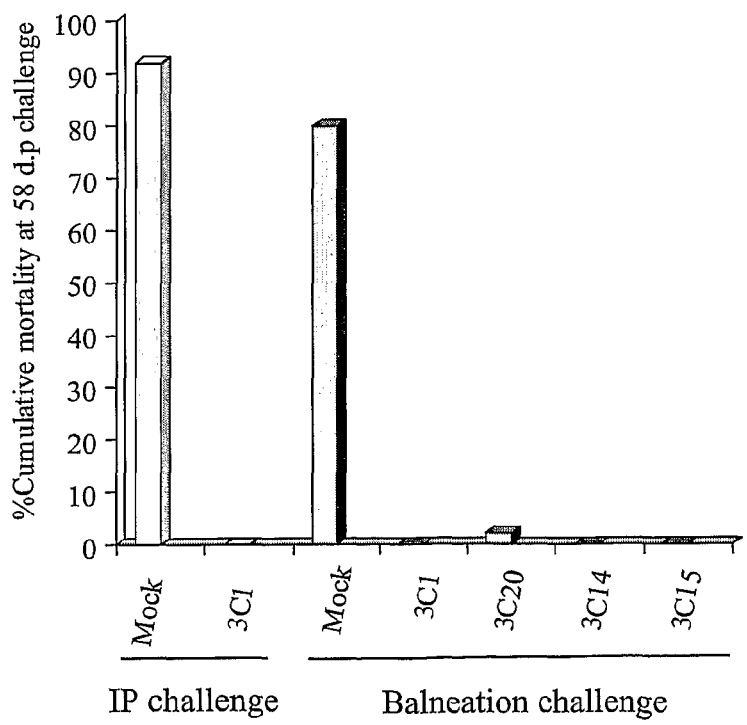
FIG. 15 shows the results from cases of challenge by balneation and challenge by injection.

The results are shown in FIG. 15.

In the case of challenge by balneation, 100% of the challenged trouts immunized with IHNV 3C1, 3C20, 3C14, or 3C15, and 98% of those immunized with IHNV 3C20 survive the challenge, while only 20% of the mock immunized trouts survive.

In the case of the challenge by injection, 100% of the challenged trouts immunized with IHNV 3C1 survive, while only 6% of the mock immunized trouts survive.

EXAMPLE 8

Use of Recombinant IHNV System as a Vaccine Vector in Mammalian Species

Replication of Recombinant IHNV in Cultured Cells from Various Species

EPC cells, as well as cells from various higher vertebrates species (human lung epithelial cells A549; porcine kidney cells PK15; rabbit kidney cells RK13; mouse fibroblasts 3T3; intestine chick embryo Cells CEV-I (ATCC CRL10495) are infected with recombinant IHNV-LUC at high multiplicity of infection (5 PFU/cell). The cells are incubated at 14 and 28° C. for three days.

At the end of the incubation time the luciferase expression is measured using a luminometer and the *Renilla* luciferase Assay system (Promega) following the manufacturer's protocol.

Figures 16, 17:
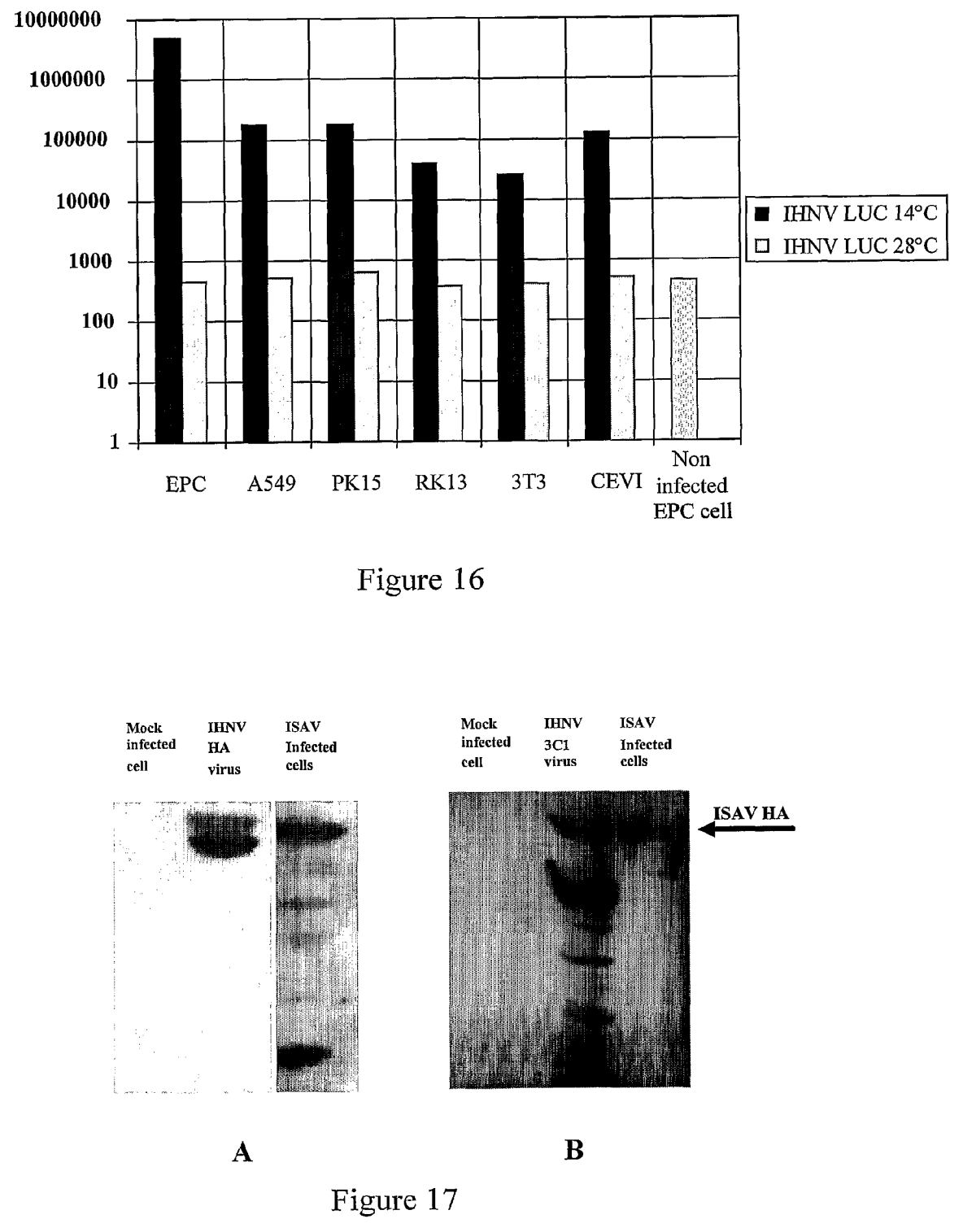

The results are shown on FIG. 16.

The light intensity, which is represented on the Y-axis in Luciferase Units (RLU), is proportional to the luciferase concentration in the cell lysate and thus to the viral replication. The luminescence detected in the non-infected cells corresponds to the background luminescence caused by nonenzymatic oxidation of the *Renilla* substrate coelenterazine.

These results show that significant replication of recombinant IHNV-LUC does occurs in several cell lines at 14° C. compared with the replication in the fish cells EPC. However, at 28° C. the cells tested including the EPC cells are unable to replicate the IHNV-LUC virus.

Administration of Recombinant IHNV In Vivo in Mice

To test the replication of IHNV in living mammals, mice are inoculated with a large amount of recombinant IHNV-LUC virus ($5.10^8$ pfu/mouse).

28 days after inoculation, the luciferase activity in the sera of mice is checked. No luciferase activity is detected, confirming the results obtained in the cell cultures.

Thus, IHNV is indeed a naturally inactivated virus in higher vertebrates.

In a second experiment, 15 mice are inoculated intra-dermal with the recombinant IHNV 3C1 (HA/F5/LUC) (1 µg of purified virus/mouse) 5 control mice receive the TNE buffer. Four weeks post-inoculation the serum from the inoculated mice was tested for the presence of antibody response against wild type IHN virus using ELISA test with a plate coated with purified IHN virus.

15 out of 15 mice inoculated with recombinant IHNV 3C1, and none of the 5 mice in the control group tested seropositive for IHNV.

Further, the serum of one of the mice inoculated with recombinant IHNV 3C1 diluted at 1/500 was tested in Western blot against a lysate of ISAV infected cells, a lysate of mock infected cells, and a whole protein extract of recombinant IHNV-HA.

As a control, a polyclonal antibody directed against the HA glycoprotein of ISAV diluted at 1/500 was tested in Western blot against the same antigens.

The results are shown on FIG. 17.

A: Western blot with the polyclonal antibody directed against the HA glycoprotein of ISAV;

B: Western blot with the serum of mice inoculated with recombinant IHNV 3C1.

These results show that the serum of the inoculated mice contains antibodies directed against different proteins of IHNV 3C1, and in particular, contains antibodies directed against the HA glycoprotein of the ISA virus.

Thus the IHNV system offers the possibility to economically produce high levels of antigens that will be safely presented in their native form for vaccination of mammalian species against diverse pathogens.

The invention claimed is:

1. A recombinant DNA construct consisting of:
   a) a transcriptional termination/polyadenylation sequence of novirhabdovirus M gene as set forth in the nucleotide sequence of SEQ ID NO: 4;
   b) a transcription initiation sequence of novirhabdovirus G gene as set forth in the nucleotide sequence of SEQ ID NO: 5;
   c) a non-transcribed intergenic dinucleotide of a novirhabdovirus preceded by said transcriptional termination/polyadenylation sequence, or followed by said transcription initiation sequence; and
   d) an open reading frame encoding a protein of interest.

2. An antigenomic cDNA of the genome of a novirhabdovirus, comprising one or more recombinant DNA constructs claim 1, inserted in said cDNA between a stop codon of a first endogenous ORF and a start codon of a second endogenous ORF of the host novirhabdovirus.

3. A recombinant novirhabdovirus containing a genomic RNA complementary to the antigenomic cDNA of claim 2.

4. An antigenomic cDNA of the genome of a novirhabdovirus, comprising three recombinant DNA constructs of claim 1, inserted in said cDNA between a stop codon of a first endogenous ORF and a start codon of a second endogenous ORF of the host novirhabdovirus.

5. A recombinant novirhabdovirus containing a genomic RNA complementary to the antigenomic cDNA of claim 4.

6. The recombinant novirhabdovirus of claim 5, wherein the recombinant novirhabdovirus is a recombinant Infectious Hematopoietic Necrosis Virus (IHNV).

7. A method of producing a protein of interest comprising expressing the recombinant novirhabdovirus of claim 3 in vertebrate cells in culture.

8. A live attenuated vaccine comprising the recombinant novirahbdovirus of claim 3.

9. An antigen delivery system for vaccination of a bird or mammal comprising the recombinant novirhabdovirus of claim 3.

10. A method for expressing an antigenic protein of interest in vitro in a low temperature expression system, comprising expressing a recombinant of IHNV or Viral Harmorrhagic Septicemia Virus (VHSV) comprising at least one recombinant DNA construct of claim 1, wherein the open reading frame encoding a protein of interest encodes said antigenic protein.

11. A low temperature in vitro expression system, wherein said expression system comprises a recombinant IHNV or VHSV, comprising at least one recombinant DNA construct of claim 1, wherein the open reading frame encoding a protein of interest encodes an antigenic protein of interest, and a vertebrate cell susceptible of infection by said recombinant virus and grows at low temperature.

12. A method for expressing in vitro an antigenic protein of interest, comprising:
   a) infecting a vertebrate cell susceptible of infection by IHNV or VHSV and which grows at low temperature with a recombinant IHNV or VHSV comprising at least one recombinant DNA construct of claim 1, wherein the open reading frame encoding a protein of interest encodes an antigenic protein of interest;
   b) culturing said cell at a temperature of about 14° C. to about 20° C.; and
   c) recovering the antigenic protein of interest produced by said cell.

13. An antigenomic cDNA of the genome of a novirhabdovirus, comprising two recombinant DNA constructs of claim 1, inserted in said cDNA between a stop codon of a first endogenous ORF and a start codon of a second endogenous ORF of the host novirhabdovirus.

* * * * *

SEQUENCE LISTING

```
<160> NUMBER OF SEQ ID NOS: 12

<210> SEQ ID NO 1
<211> LENGTH: 22
<212> TYPE: DNA
<213> ORGANISM: Infectious hematopoietic necrosis virus

<400> SEQUENCE: 1
ccaagacaga aaaaaatggc ac                                                  22

<210> SEQ ID NO 2
<211> LENGTH: 16
<212> TYPE: DNA
<213> ORGANISM: Infectious hematopoietic necrosis virus

<400> SEQUENCE: 2
ccaagacaga aaaaaa                                                         16
```

-continued

<210> SEQ ID NO 3
<211> LENGTH: 12
<212> TYPE: DNA
<213> ORGANISM: Infectious hematopoietic necrosis virus

<400> SEQUENCE: 3
gcacttttgt gc                                                         12

<210> SEQ ID NO 4
<211> LENGTH: 16
<212> TYPE: DNA
<213> ORGANISM: Artificial
<220> FEATURE:
<223> OTHER INFORMATION: Consensus

<400> SEQUENCE: 4
vhhagayaga aaaaaa                                                     16

<210> SEQ ID NO 5
<211> LENGTH: 12
<212> TYPE: DNA
<213> ORGANISM: Artificial
<220> FEATURE:
<223> OTHER INFORMATION: Consensus

<400> SEQUENCE: 5
gcacdwkwgt gy                                                         12

<210> SEQ ID NO 6
<211> LENGTH: 16
<212> TYPE: DNA
<213> ORGANISM: Viral hemorrhagic septicemia virus

<400> SEQUENCE: 6
attagataga aaaaaa                                                     16

<210> SEQ ID NO 7
<211> LENGTH: 12
<212> TYPE: DNA
<213> ORGANISM: Viral hemorrhagic septicemia virus

<400> SEQUENCE: 7
gcacatttgt gt                                                         12

<210> SEQ ID NO 8
<211> LENGTH: 16
<212> TYPE: DNA
<213> ORGANISM: Hirame rhabdovirus

<400> SEQUENCE: 8
atcagataga aaaaaa                                                     16

<210> SEQ ID NO 9
<211> LENGTH: 16
<212> TYPE: DNA
<213> ORGANISM: Snakehead rhabdovirus

<400> SEQUENCE: 9
gaaagacaga aaaaaa                                                     16

<210> SEQ ID NO 10
<211> LENGTH: 12
<212> TYPE: DNA
<213> ORGANISM: Snakehead rhabdovirus

```
<400> SEQUENCE: 10
gcacgagagt gc                                                                12

<210> SEQ ID NO 11
<211> LENGTH: 70
<212> TYPE: DNA
<213> ORGANISM: Artificial
<220> FEATURE:
<223> OTHER INFORMATION: Primer

<400> SEQUENCE: 11
ggggcggccg ccaagacaga aaaaaatggc acttttgtgc actagtatga cttcgaaagt           60
ttatgatcca                                                                  70

<210> SEQ ID NO 12
<211> LENGTH: 40
<212> TYPE: DNA
<213> ORGANISM: Artificial
<220> FEATURE:
<223> OTHER INFORMATION: Primer

<400> SEQUENCE: 12
ggggcggccg cccgggttat tgttcatttt tgagaactcg                                 40
```